United States Patent
Wood et al.

(10) Patent No.: US 10,342,446 B2
(45) Date of Patent: Jul. 9, 2019

(54) THERMAL POWERED MEDICAL DEVICE

(71) Applicant: Welch Allyn, Inc., Skaneateles Falls, NY (US)

(72) Inventors: Robert J. Wood, Syracuse, NY (US); Steven D. Baker, Beaverton, OR (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 1445 days.

(21) Appl. No.: 13/682,424

(22) Filed: Nov. 20, 2012

(65) Prior Publication Data
US 2013/0137957 A1 May 30, 2013

Related U.S. Application Data (60) Provisional application No. 61/565,322, filed on Nov. 30, 2011.

(51) Int. Cl.
| | |
|---|---|
| *A61B 1/227* | (2006.01) |
| *H01L 35/30* | (2006.01) |
| *A61B 5/0408* | (2006.01) |
| *A61B 5/00* | (2006.01) |
| *A61B 5/0402* | (2006.01) |

(52) U.S. Cl.
CPC .......... *A61B 5/0408* (2013.01); *A61B 1/227* (2013.01); *A61B 5/00* (2013.01); *A61B 5/0402* (2013.01); *H01L 35/30* (2013.01); *A61B 2560/0214* (2013.01)

(58) Field of Classification Search
CPC ....... A61B 5/0408; A61B 5/00; A61B 5/0402; A61B 1/227; A61B 2560/0214; H01L 35/30
See application file for complete search history.

(56) References Cited

U.S. PATENT DOCUMENTS

| | | | |
|---|---|---|---|
| 3,978,850 A * | 9/1976 | Moore | A61B 1/227 600/200 |
| 4,213,292 A | 7/1980 | Dolezal et al. | |
| 4,790,324 A | 12/1988 | O'Hara et al. | |
| 5,733,255 A | 3/1998 | Dinh et al. | |
| 6,075,199 A * | 6/2000 | Wong | H01L 35/00 136/201 |
| 6,222,114 B1 | 4/2001 | Mitamura | |
| 6,480,441 B1 * | 11/2002 | McKay | G02B 25/002 359/809 |
| 7,532,937 B2 | 5/2009 | Horio et al. | |

(Continued)

FOREIGN PATENT DOCUMENTS

| | | |
|---|---|---|
| JP | 11-206032 | 7/1999 |
| WO | WO 2009/044340 A2 | 4/2009 |

OTHER PUBLICATIONS

Dorfman, Danielle "Combined thermometer/otoscope device providing dual functionality with no external power source for developing world hospitals", May 17, 2010, Department of Biomedical Engineering, Johns Hopkins University.*

(Continued)

*Primary Examiner* — Tamir Ayad
(74) *Attorney, Agent, or Firm* — Merchant & Gould P.C.

(57) ABSTRACT

A thermal powered medical device generates power from a temperature differential between a living body and a differential temperature source. The power is supplied to power one or more electrical components of the medical device.

9 Claims, 6 Drawing Sheets

(56) References Cited

U.S. PATENT DOCUMENTS

2006/0254638 A1    11/2006   Carmeli et al.
2007/0253227 A1    11/2007   James et al.
2008/0058680 A1     3/2008   Lee et al.
2008/0139894 A1     6/2008   Szydlo-Moore et al.

OTHER PUBLICATIONS

Human++: body area networks, Scientific Report, http://www.imec.be/ScientificReport/SR2007/html/1384142.html, 3 pages (2007).

Leonov, V. et al., "Wearable electronics self-powered by using human body heat: The state of the art and the perspective," *Journal of Renewable and Sustainable Energy*, vol. 1, No. 6, Article ID 062701, 14 pages (2009).

Lossec, M. et al., "Thermoelectric generator placed on the human body: system modeling and energy conversion improvements," *The European Physical Journal Applied Physics*, vol. 52, Issue 1, 10 pages (2010).

Paradiso, J. et al., "Energy Scavenging for Mobile and Wireless Electronics," *IEEE Pervasive Computing*, vol. 4, Issue 1, pp. 18-27 (Jan.-Mar. 2005).

Stordeur, M. et al., "Low Power Thermoelectric Generator—self-sufficient energy supply for micro systems," *16th International Conference on Thermoelectrics*, pp. 575-577 (1997).

Thermocouple, *Wikipedia, the free encyclopedia*, 5 pages (Oct. 5, 2011).

Thermoelectric Generator, http://www.tegpower.com, .2 pages (Oct. 12, 2011).

\* cited by examiner

THERMAL POWERED MEDICAL DEVICE

CROSS-REFERENCE TO RELATED APPLICATION

This application claims priority to U.S. Ser. No. 61/565,322, titled THERMAL POWERED MEDICAL DEVICE, filed on Nov. 30, 2011, which is hereby incorporated by reference in its entirety.

BACKGROUND

Devices that require electric power are commonly powered by a power cord connected to a wall receptacle or by a battery power supply. Power cords are often undesirable because they reduce the portability of such devices. Battery power supplies permit devices to be portable, but still require at least occasional replacement or recharging of the batteries. When recharging, the devices are often connected to a wall receptacle or placed into a power cradle, which is itself connected to a wall receptacle. Accordingly, even when a battery power supply is used, connection to a wall receptacle or other external power source is often still required in order to charge the batteries. Devices that do not require charging or connection to an external power source are desired.

SUMMARY

In general terms, this disclosure is directed to a thermal powered medical device. In one possible configuration and by non-limiting example, the medical device is powered by heat from the body of a living creature.

One aspect is a device comprising: a thermoelectric device having a first portion and a second portion and operable to generate a low-voltage output from a temperature differential; a heat source interface device thermally coupled to the first portion of the thermoelectric device and configured to be placed in contact with a portion of a living body having a first temperature; a differential temperature source thermally coupled to the second portion of the thermoelectric device and configured to have a second temperature different than the first temperature, wherein the temperature differential is the difference between the first and second temperatures; and a boost circuit electrically coupled to the thermoelectric device and the electrical component, wherein the boost circuit is configured to boost the low-voltage output to a higher-voltage output to power an electrical component.

Another aspect is a method of powering an electrical component, the method comprising: receiving heat from a portion of a living body with a heat source interface device, the portion of the living body having a first temperature, wherein the heat generates a temperature differential between the heat source interface device and a differential temperature source having a second temperature; generating a low-voltage output with a thermoelectric device from the temperature differential between the first temperature and the second temperature, the thermoelectric device coupled to the heat source interface device and the differential temperature source; and boosting the low-voltage output to a higher voltage output with a boost circuit electrically coupled to the thermoelectric device; and powering an electrical component with the higher voltage output.

A further aspect is a handheld medical device, comprising: an instrument including at least one electrical component; and a power handle comprising: a mechanical interface configured to selectively connect the power handle to the instrument; an electrical interface configured to electrically connect the power handle to the electrical component when the power handle is connected to the instrument; a solid metallic inner core having an outer surface, the inner core encompassing at least a majority of the volume of the power handle; a plurality of thermocouples having a first portion thermally connected to the outer surface of the inner core; at least one thermally conductive layer connected to a second portion of the thermocouples, opposite the inner core, wherein the thermally conductive layer forms at least part of an exterior of the power handle; and a boost circuit electrically coupled to the thermocouples and to the electrical interface, wherein the boost circuit is configured to receive electrical energy generated by the thermocouples and to boost a voltage of the electrical energy to power the at least one electrical component.

DETAILED DESCRIPTION

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

Figure 1:
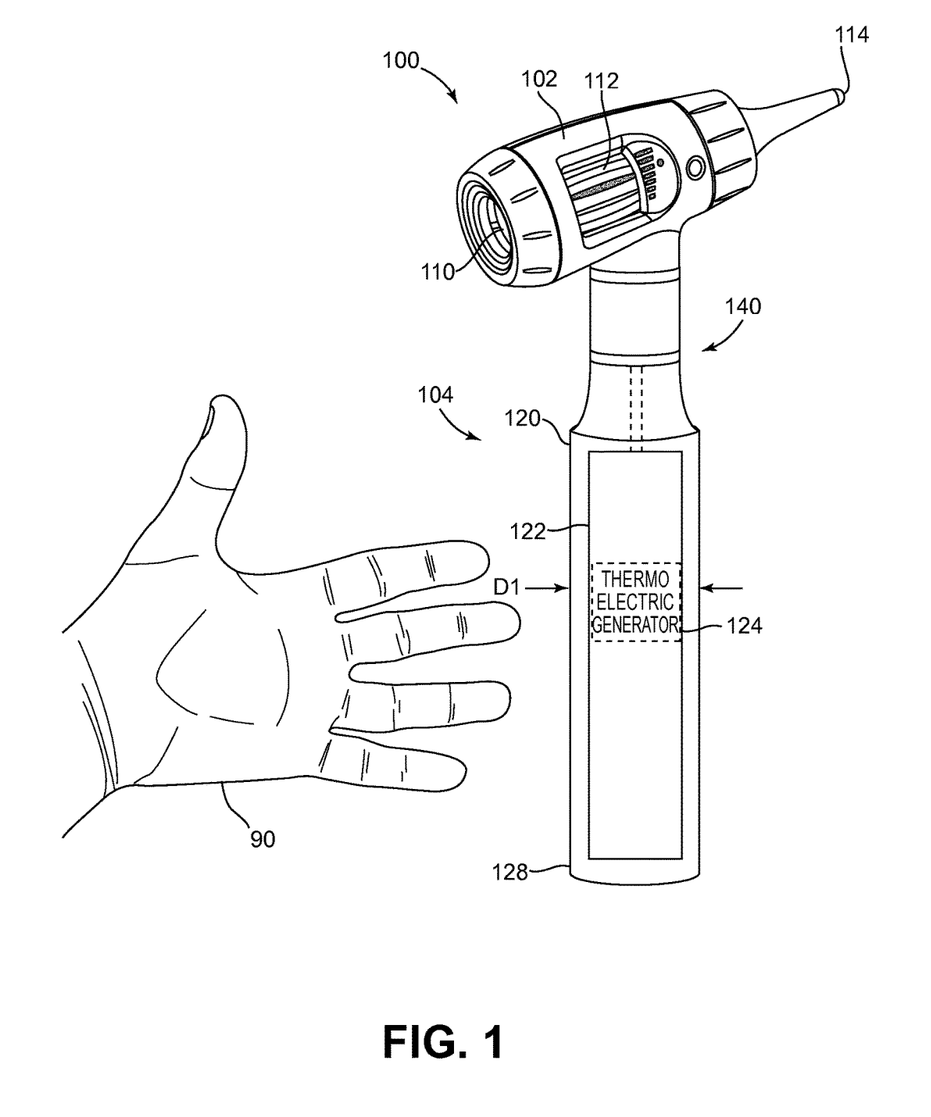
FIG. 1 illustrates an example thermal powered device in the form of a handheld medical device.

FIG. 1 is a schematic perspective view of an example thermal powered device, and more specifically an example of a handheld medical device 100. In this example, the handheld medical device 100 includes an instrument 102 and a power handle 104. The handheld medical device 100 is configured to be held in a hand 90.

An example of instrument 102 is an otoscope, which includes an adjustable optics assembly 110, an adjustment control 112, and an electrical component, such as a light source 114. An otoscope can be used by a healthcare provider during a patient encounter to view inside a patient's ear canal. To do so, the healthcare provider inserts the end of the otoscope into the ear canal, where it is illuminated by the light source 114. The healthcare provider then looks through the optics assembly 110 and adjusts the focus, if necessary, using the adjustment control 112. As discussed below, the light source 114 is powered by a thermoelectric generator in the power handle 104. Power is transferred through conductors within the instrument 102.

A wide variety of instruments 102 can be used in other embodiments. In some embodiments, the instrument 102 is a medical examination instrument, such as an otoscope, an ophthalmoscope, a thermometer, a sphygmomanometer, a skin surface microscope, a unidirectional occluder, an examination light, an electronic stethoscope, a tympanometric instrument, an audiometer, or a variety of other medical examination instruments. Another example of an instrument 102 is a heart monitor (such as an electrocardiogram (EKG) instrument. In other embodiments, the instrument 102 is a therapeutic device, such as a surgical instrument, a drug delivery or measurement instrument, or other therapeutic devices. Although exemplary embodiments are described as handheld medical devices, other embodiments are possible, such as non-handheld devices, or non-medical devices.

The power handle 104 forms a handle for the medical device 100, and is sized to be held in the hand 90 of the healthcare provider. In this example, the power handle 104 includes a housing 120 and thermoelectric circuitry 122 within the housing 120. The thermoelectric circuitry 122 includes, for example, a thermoelectric generator 124. In some embodiments, the thermoelectric circuitry 122 forms part of the housing 120.

The housing 120 is, in some embodiments, sized and configured to be held by a hand 90 of a healthcare provider. The housing 120 is typically formed of materials such as metal or plastic, and forms a protective enclosure for at least some of the thermoelectric circuitry 122 contained within the housing 120. In some embodiments, portions of the thermoelectric circuitry 122 are exposed outside of the housing 120, as discussed herein.

In some embodiments, the housing 120 has a cross-sectional dimension D1 sized to fit within a hand 90 of a healthcare provider. In one example, the dimension D1 is in a range from about 0.5 inches to about 4 inches. In another example, the dimension D1 is in a range from about 0.5 inches to about 0.2 inches. In yet another example, the dimension D1 is about one inch. In some embodiments, at least a portion of the housing 120 has a cylindrical shape, in which case the dimension D1 is the diameter of the housing 120.

In some embodiments, the housing 120 of the power handle 104 is sealed. A sealed housing 120 reduces the chance of water or other liquid or particle intrusion into the interior of housing 120. A sealed housing 120 is also easier to clean and sanitize.

In some embodiments, the thermoelectric circuitry 122 acts as a power source for the instrument 102. The thermoelectric circuitry 122 includes, for example, a thermoelectric generator 124.

The thermoelectric generator 124 generates electrical energy from a temperature differential. For example, when the handheld medical device 100 is grasped in a hand 90 of an operator, heat from the hand 90 is used to generate the electrical energy. Examples of the thermoelectric circuitry and the thermoelectric generator 124 are illustrated and described in more detail herein.

In some embodiments the instrument 102 is connected to the power handle 104 at an interface 140. The interface 140 typically includes a mechanical interface, such as mating screw threads, or a snap together connection, and also an electrical interface to transfer power from the power handle 104 into the instrument 102. In some embodiments the instrument 102 can be disconnected from the power handle 104 at the interface 140. The interface 140 can be used in a variety of different types of instruments, to permit a single configuration of power handle 104 to be used with multiple different types of instruments. In other possible embodiments, however, instrument 102 is a single unit that includes the components of the power handle 104 within the housing 120 of instrument 102, rather than within a separate power handle.

The hand 90 is one example of a portion of a living body that can be used as a heat source to generate a temperature differential. In some embodiments, the hand 90 is a portion of a human. Other embodiments utilize other parts of a human as a heat source, such as a head, a neck, an arm, a wrist, a hand, a shoulder, an underarm, a back, a stomach, a hip, a leg, a foot. Yet other embodiments utilize a part of another living creature. For example, some embodiments utilize a part of a mammal or a bird. In some embodiments the creature is warm-blooded. In some embodiments, the living creature has a relatively higher blood temperature, and maintains thermal homeostasis primarily through internal metabolic processes.

Figure 2:
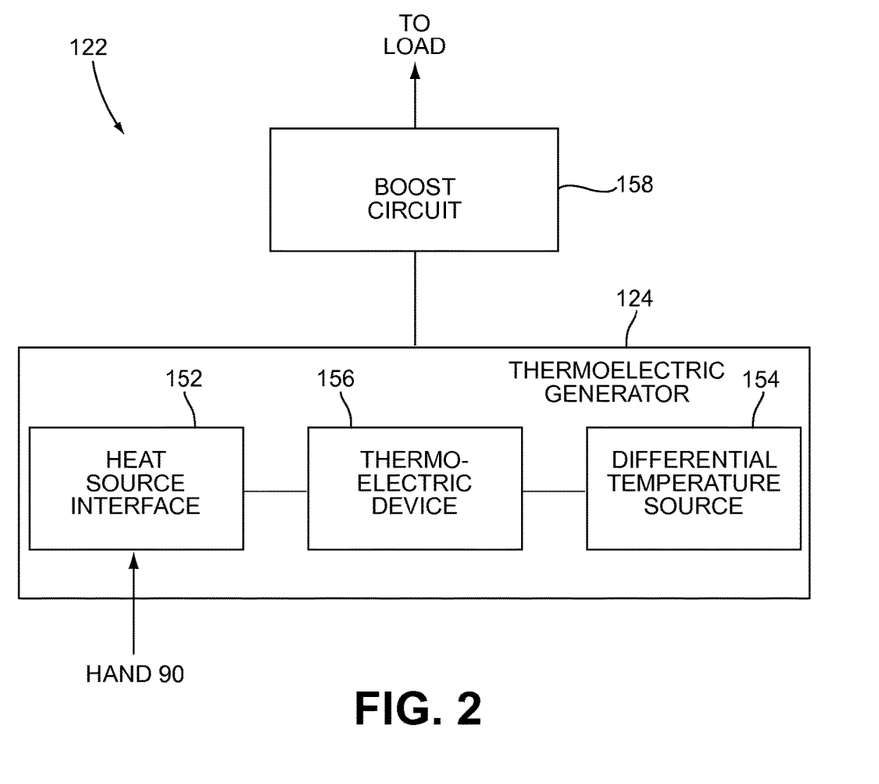
FIG. 2 is a schematic block diagram illustrating an example of thermoelectric circuitry.

FIG. 2 is a schematic block diagram illustrating an example of thermoelectric circuitry 122. In this example, the thermoelectric circuitry 122 includes a thermoelectric generator 124 and boost circuit 158.

The thermoelectric generator 124 operates to generate electrical energy from a temperature differential. The electrical energy is then boosted by boost circuit 158.

In this example, the thermoelectric generator 124 includes the heat source interface 152, the differential temperature source 154, and the thermoelectric device 156.

The heat source interface 152 receives heat from a heat source. The heat source is typically an external heat source, such as a portion of a living body, having a first temperature (e.g., 90 degrees F.). In this example, the portion of the living body is the hand 90 (shown in FIG. 1). The heat source interface 152 is configured to collect heat from the hand 90, so that upon engagement of the hand 90 with the heat source interface 152, the heat source interface 152 is quickly warmed by the hand 90 to approximately the first temperature.

In order to be quickly warmed, the heat source interface 152 is typically formed of a thermally conductive material having a relatively low mass. An example of a thermally conductive material is a metal. Some embodiments utilize one or more thin layers of metal. Other embodiments utilize other metals, such as copper, gold, or steel, or alloys of these or other metals. A mass of the heat source interface 152 is preferably much less than a mass of the differential temperature source 154, and also preferably much less than a mass of the hand 90, or other heat source.

The differential temperature source 154 is coupled to the thermoelectric device 156 to generate a temperature differential with the heat source interface 152, when the heat source interface 152 is engaged with the hand 90, or other heat source. Accordingly, the differential temperature source 154 preferably has a different temperature than the hand 90 during use.

In some embodiments, the differential temperature source 154 is a metallic core having a relatively large mass. In some embodiments, the metallic core encompasses at least a majority of the volume of the power handle 104. When exposed to the ambient atmosphere over time, the metallic core will acquire a temperature approximately equal to the temperature of the ambient atmosphere. When the ambient atmosphere is at a second temperature, the metallic core will acquire a temperature approximately equal to the second temperature. (For example, if the ambient atmosphere is room temperature, the second temperature may be about 70 degrees F.)

When the heat source interface 152 is engaged by the hand 90, heat begins to be transferred from the heat source interface 152 to the differential temperature source 154. The greater the mass of the differential temperature source 154, the longer it will take for the temperature of the differential temperature source 154 and the heat source interface 152 to become approximately the same. Accordingly, the greater the mass of the differential temperature source 154, the longer the thermoelectric generator 124 will continue to generate electrical energy.

On the other hand, a differential temperature source 154 having a large mass results in a heavier handheld medical device 100. Accordingly, the mass should be selected to be large enough to generate electrical energy for a suitable period of time, without being so large as to make the handheld medical device 100 difficult to handle and use. In one example, the metallic core differential temperature source 154 has a mass in a range from about 0.05 kg to about 0.5 kg.

An example of a handheld medical device 100 including a metallic core differential temperature source 154 is illustrated in more detail with reference to FIG. 3.

In another embodiment, the differential temperature source 154 is a device that interfaces with another heat source. For example, in some embodiments the differential temperature source 154 is a heat sink that interfaces with the ambient atmosphere, or other gas. In another example embodiment, the differential temperature source 154 is a heat sink that interfaces with a liquid, such as water. In another example embodiment, the differential temperature source 154 is a device configured to be coupled to another object.

An example of a medical device 100 having a heat sink differential temperature source 154 is illustrated and described in more detail with reference to FIG. 5.

Typically the differential temperature source 154 has a second temperature that is less than the first temperature of the hand 90 (or other heat source). In another embodiment, however, the differential temperature source 154 has a second temperature that is greater than the first temperature. So long as the temperatures are sufficiently different, the thermoelectric generator 124 is operable to generate the electrical energy.

The thermoelectric device 156 generates electrical energy from the temperature differential between the heat source interface 152 and the differential temperature source 154. The thermoelectric device 156 is typically coupled to the heat source interface 152 at a first side, and to the differential temperature source 154 at the other side, opposite the first side.

An example of a thermoelectric device 156 is a thermocouple. A thermocouple typically includes two conductors formed of dissimilar metals. In some embodiments, the conductors are metal alloys. One example is a Type J thermocouple, formed of iron and constantan (a copper-nickel alloy, such as having about 55% copper and 45% nickel). Another example is a Type K thermocouple, formed of chromel (a nickel chromium alloy, such as having about 95% nickel and about 10 percent chromium) and alumel (an alloy having about 95% nickel, 2% manganese, 2% aluminum, and 1% silicon). Some embodiments include a combination of multiple types of thermocouples, such as a combination of Type J and Type K thermocouples). When opposing ends of the conductors are connected to the heat source interface 152 and the differential temperature source 154, a temperature differential is formed across the conductors. The thermocouple then generates a voltage proportional to the temperature difference. Some thermocouples are formed of semiconductors, such as n-type and p-type semiconductor materials.

Although the electrical energy generated by a single thermocouple may be small, the thermoelectric device 156 can include a plurality of thermocouples to multiply the electrical energy generated. For example, if a single thermocouple generates an output of 1 millivolt for a given temperature differential, one hundred thermocouples can be arranged in series to generate 100 millivolts, and two or three hundred thermocouples can arranged to generate 200 or 300 millivolts.

In some embodiments, the thermoelectric device 156 includes one or more thermopiles. A thermopile is, for example, an electronic device that is composed of multiple thermocouples.

In some embodiments, the thermoelectric device 156 includes one or more peltier coolers, such as the model number 9501/031/030 B peltier cooler available from Ferrotec (USA) Corporation of Santa Clara, Calif. A peltier cooler is an example of a thermopile. In this example, the peltier cooler is a 31-couple, 3-amp module. The 'B' code indicates that this thermoelectric cooler features a lapped type, plain ceramic surface. In some embodiments, the peltier cooler has a length and a width in the range from about 10 mm to about 20 mm, and in some embodiments about 15 mm; and a height in a range from about 1 to about 10 mm, and in some embodiments about 3 mm.

Additionally, some embodiments of the peltier cooler include a high reliability, lead-free, 200 degree Celsius maximum process temperature, with a 3-amp maximum current. Some embodiments are in the shape of a single-stage module. Other embodiments utilize peltier coolers with other characteristics, features, or configurations.

The output of the thermoelectric generator 124 is provided by electrical conductors to the boost circuit 158 through the electrical coupling between the thermoelectric device 156 and the boost circuit 158.

Figure 3:
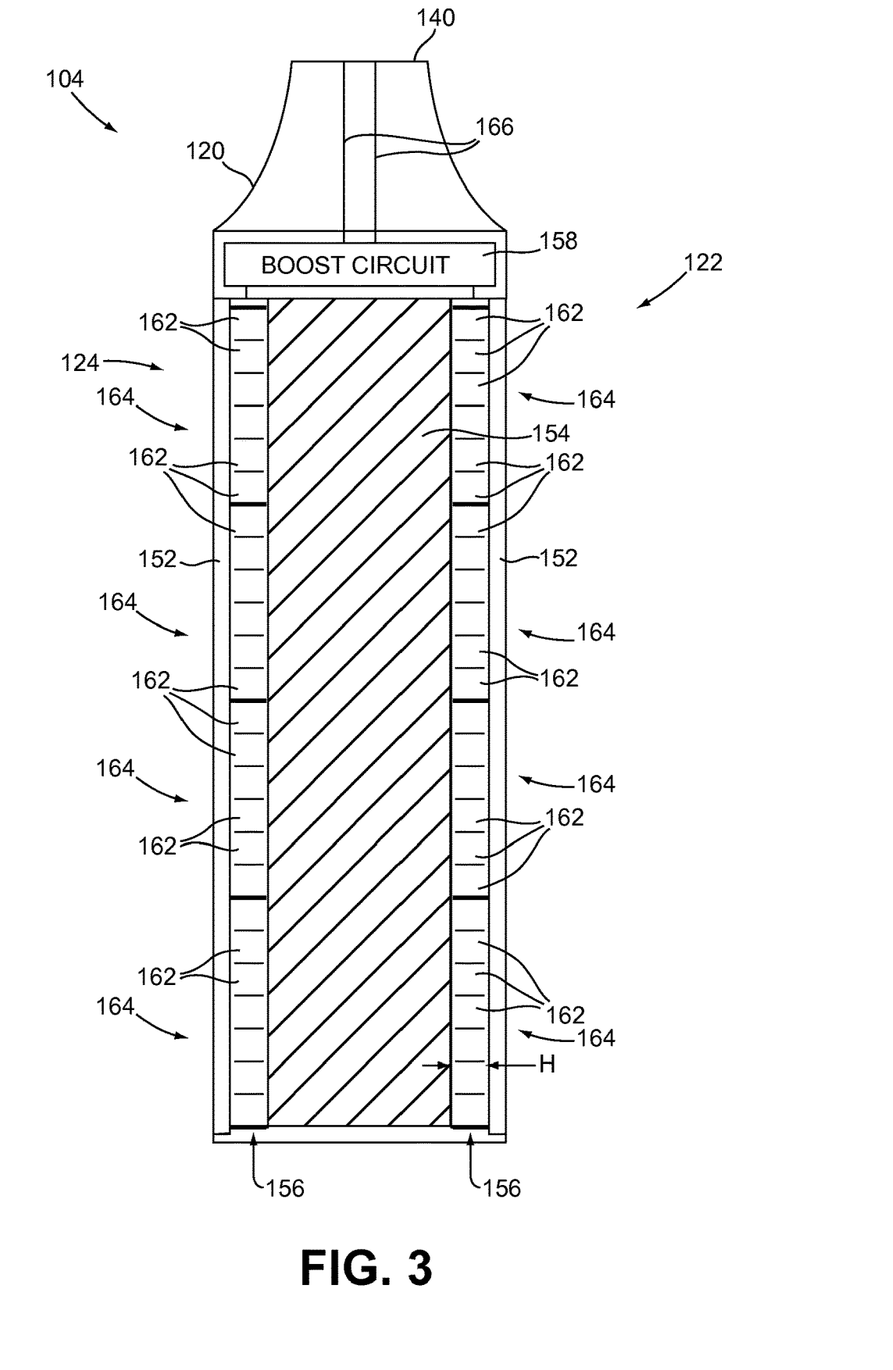
FIG. 3 is a schematic cross-sectional view of an example power handle of a handheld medical device.

The output of the boost circuit 158 is provided to the load by electrical conductors, such as the electrical conductors 166, shown in FIG. 3. A wide variety of loads can be powered by the output, such as the instrument 102 (shown in FIG. 1) or the electrical component 192 (shown in FIG. 5).

FIG. 3 is a schematic cross-sectional view of an example power handle 104 of the handheld medical device 100, shown in FIG. 1. In this example, the power handle 104 includes a housing 120, interface 140, and thermoelectric circuitry 122. The thermoelectric circuitry 122 includes thermoelectric generator 124 and boost circuit 158. The thermoelectric generator 124 includes heat source interface 152, differential temperature source 154, and thermoelectric device 156.

In this example, the differential temperature source 154 is a metallic core. An example of a metallic core is a solid piece of aluminum. Other metals are used in other embodiments. In one example, the metallic core has roughly a rectangular longitudinal cross section and roughly a square transverse cross section. This shape interfaces well with square-shaped thermopiles with flat opposing surfaces. In another possible embodiment, the metallic core is cylindrical. In this embodiment, curved thermopiles are used, or alternatively, thermocouples can be arranged in a radial configuration around the cylindrical core. Other configurations can also be used in other embodiments.

The thermoelectric device 156 is positioned adjacent to the differential temperature source 154, such that one side of the thermoelectric device 156 is thermally coupled to the differential temperature source 154. In some embodiments the thermoelectric device 156 is in direct contact with an exterior surface of the differential temperature source 154. A fastener is used in some embodiments to connect the thermoelectric device 156 to the differential temperature source 154, such as a thermally conductive adhesive, weld joints, screws, tape, etc.

As discussed herein, the thermoelectric device 156 typically includes multiple or many thermocouples 162. In some embodiments, the thermoelectric device 156 includes a plurality of thermopiles 164, each including multiple thermocouples 162. A thermopile 164 is sometimes referred to as a thermoelectric cooler, or a Peltier device. An example of a thermopile 164 is the model number 9501/031/030 B peltier cooler, described herein.

As illustrated in FIG. 3, multiple thermopiles 164 can be arranged about the periphery of differential temperature source 154. The multiple thermopiles 164 can include multiple thermocouples 162 arranged in series, and the multiple thermopiles 164 are also arranged in series. In this way, the voltage generated by the thermocouples is added together to generate a much larger voltage than can be generated by the individual thermocouples.

In some embodiments, the thermopiles 164 have widths and lengths of approximately 0.5 inches to about 2 inches, and preferably about one inch. In some embodiments, the thermopiles 164 have a height (H) in a range from about 0.05 inches to about 0.3 inches, and preferably about 0.15 inches. Other embodiments include thermopiles having other shapes and dimensions.

In the illustrated example, the differential temperature source 154 is a solid metallic core having a square cross-sectional shape, with four sides. Thermopiles 164 are positioned on each side in vertical rows. In some embodiments, each row includes a quantity of thermopiles 164 from 1 to 20, and preferably about 4 to 8. Some embodiments include about 6 thermopiles 164 in each row. In this example, the thermoelectric device 156 includes a total quantity of thermopiles 164 (on all four sides) in a range from 4 to 80, and preferably from about 16 to 32. Some embodiments include about 24 thermopiles 164. More or fewer thermopiles 164 are used in other embodiments. For example, some embodiments include one or more thermopiles.

Because each thermopile includes multiple thermocouples, the thermoelectric device 156 includes many thermocouples. In some embodiments, the thermoelectric device 156 includes a plurality of thermocouples, such as at least 50, 100, 200, 500, or 1000 thermocouples.

The heat source interface 152 is also arranged so that it is in thermal communication with the thermoelectric device 156, opposite the differential temperature source 154. In this example, the heat source interface 152 is one or more thin layers of a thermally conductive material. As one example, the heat source interface 152 is aluminum tape that is wrapped around the thermopiles 164, having at least one metallic layer and a thin adhesive coating. The aluminum tape provides a thin thermally conductive exterior surface. The aluminum tape also acts as the fastener to connect the heat source interface 152 to the thermoelectric device 156, and also as the fastener to connect the thermoelectric device 156 to the differential temperature source 154. In an example embodiment, the heat source interface 152 has a thickness in a range from about 0.01 inches to about 0.2 inches. In some embodiments, a mass of the heat source interface 152 is at least 10 times less than a mass of the differential temperature source 154. In other possible embodiments, the mass is at least 50 times, 100 times, 200 times, 300 times, or 1000 times less. Other embodiments have other thicknesses or configurations.

In another embodiment, the heat source interface 152 is a thin layer of thermally conductive material, such as a metallic material. In some embodiments, the heat source interface 152 is connected to the thermoelectric device 156 by a fastener, such as those disclosed herein.

The heat source interface 152 typically has a mass that is much less than a mass of the metallic core differential temperature source 154. This permits the heat source interface 152 to warm rapidly when the heat source (such as hand 90, shown in FIG. 1) is placed in contact with it, to provide a temperature differential across the thermoelectric device 156.

Prior to operation, the handheld medical device 100 is typically exposed to the ambient atmosphere. In an interior space, such as a hospital or clinic examination room, the interior space has a room temperature commonly around 70 degrees F. If the handheld medical device 100 is not exposed to other heat sources for a period of time, the differential temperature source 154 will obtain a temperature of approximately room temperature. However, rooms may have significantly different temperatures. In addition, the handheld medical device 100 could also be used outdoors, where temperatures could vary significantly.

When an operator desires to use the handheld medical device 100, the operator grasps the handheld medical device 100 with a hand 90. A human body maintains a relatively consistent internal temperature of about 97 to 99 degrees. Temperatures of limbs of the body can be somewhat less than the internal temperature. For example, the temperature of hand 90 may be about 10 degrees cooler than the internal temperature, or approximately 85 to 90 degrees. Contact between the hand 90 and the heat source interface 152 causes heat to be transferred to the heat source interface. The relatively low mass of the heat source interface 152 permits the heat source interface 152 to heat up rapidly, so that the temperature of the heat source interface 152 is approximately the same as the temperature of hand 90, or about 85-90 degrees.

A temperature differential is formed between the heat source interface 152 (e.g., 90 degrees) and the differential temperature source 154 (e.g., 70 degrees). The thermoelectric device 156 operates to generate electrical energy from the temperature differential. The amount of electrical energy generated by the thermoelectric device 156 is a function of the temperature difference, and also a function of the number and qualities of the thermocouples 162 (FIG. 3). In some embodiments, the thermoelectric device 156 generates electrical energy having an electric potential of greater than 20 mV. In some embodiments, the output is in a range from about 20 mV to about 200 mV.

The thermoelectric device 156 continues to generate electrical energy so long as a suitable temperature differential exists between the heat source interface 152 and the differential temperature source 154. In some embodiments, the suitable temperature differential is at least 5 degrees. Other embodiments can continue to operate with lower temperature differentials.

In addition, because the output of the thermoelectric generator 124 varies with the magnitude of the temperature difference between the differential temperature source 154 and the heat source interface 152, the power handle 104 can be designed to provide a variable output based on grip strength or magnitude of surface area contact. For example, if the heat source interface 152 is gripped very lightly by hand 90, the temperature of the heat source interface will be lower than if it is gripped tightly. As a result, the output can be adjusted by gripping the heat source interface more tightly or more loosely.

Similarly, by adjusting the magnitude of surface area contact, the output can be adjusted. For the greatest output, the heat source interface 152 can be gripped with the entire palm and fingers of one hand 90, or even with two hands. The output can be reduced by providing a smaller surface area, such as by removing several fingers, or by gripping the heat source interface 152 with only the finger tips.

If the difference in temperatures between the heat source interface 152 and the differential temperature source 154 becomes less than the suitable temperature differential, the temperature of the differential temperature source 154 can be adjusted. For example, the power handle 104 can be set down to allow the differential temperature source 154 to return to room temperature. Alternatively, the temperature can be adjusted by cooling the power handle 104, such as by placing the power handle 104 in cooler water, in a refrigerator or other cool location, etc. The temperature could also be elevated by heating the power handle 104, such as by placing the power handle 104 over or near a fire, in warmer water, in an oven or other warm or hot location, etc. Once the differential temperature source 154 has been warmed or cooled to a suitable temperature, the power handle 104 can be returned to operation.

In some embodiments, the thermoelectric generator 124 can continue to generate electricity for a period of time. In some embodiments, the period of time is greater than 10 seconds, 30 seconds, 1 minute, 10 minutes, or 30 minutes.

In addition, some embodiments include a power switch. When the power switch is off, the one or more electronic components in the instrument 102 are not powered, but energy generated by the thermoelectric generator 124 can continue to be collected. For example, a capacitor can be used to store the electrical energy. In some embodiments, the electrical energy is stored in a high capacity capacitor, such as a super capacitor or an ultra capacitor. The electrical energy can then be supplied to the electronic component from the capacitor once the power switch is turned on.

The boost circuit 158 is electrically coupled to the thermoelectric device 156 to receive the electrical energy generated by the thermocouples 162. Electrical conductors (not shown) are typically used to conduct the electrical energy between the thermoelectric device 156 and the boost circuit 158. In this example, the boost circuit 158 is positioned toward the upper end of the power handle 104, near the instrument interface 140. An example of a boost circuit 158 is illustrated and described in more detail with reference to FIG. 4. The output of the boost circuit 158 is provided to the interface 140 with electrical conductors 166. In some embodiments, the boost circuit 158 provides an output having an electrical potential that is more than 10 times, 50 times, 100 times, or 200 times the electrical potential from the thermoelectric device 156. For example, in some embodiments the output voltage is in a range from 2 volts to 5 volts.

In some embodiments, the thermoelectric circuitry 122 powers one or more electronic components of the handheld medical device 100. An example of an electronic component is a bulb 114. Some bulbs require a certain voltage in order to operate. For example, a 3.5V bulb may require an electric potential of at least 3.5V in order to operate. In some embodiments, the thermoelectric circuit generates at least 3.5V. Other embodiments provide other electric potentials in order to power other electronic components.

Figure 4:
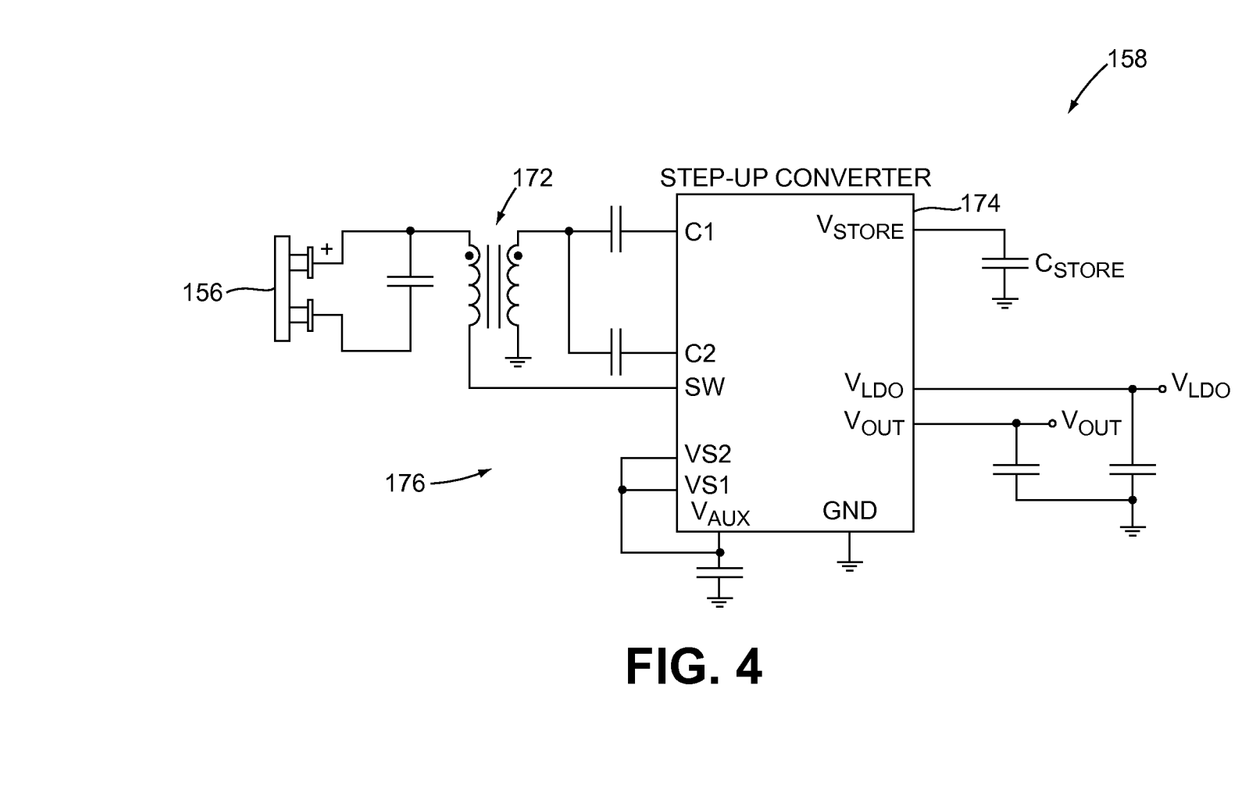
FIG. 4 is a schematic block diagram of an example boost circuit.

FIG. 4 is a schematic block diagram of an example boost circuit 158. In this example, the boost circuit 158 includes a step-up transformer 172, step-up converter 174, and supporting electronic circuitry 176.

The step-up transformer 172 receives electrical energy from the thermoelectric device 156 and boosts the voltage. For example, a 1:100 ratio step-up transformer 172 is used in some embodiments to increase the voltage from the primary winding by a factor of 100 at the secondary winding. Other ratios can be used in other embodiments, such as ratios in a range from about 1:10 to about 1:1000. The boosted voltage is supplied to the step-up converter through blocking capacitors at pins C1 and C2. The SW pin is connected to the primary winding, to control current flow through the primary winding.

The step-up converter 174 operates to increase the voltage of the electrical energy from the transformer 172 (which received its energy from the thermoelectric device 156) to a higher voltage ($V_{OUT}$). An example of the step-up converter 174 is an ultralow voltage step-up converter and power manager chip, part number LTC3108, available from Linear Technology Corporation of Milpitas, Calif.

The thermoelectric device 156, which may be one or more thermopiles 164 (multiple thermopiles can be arranged in parallel or in series, as appropriate), generates electrical energy that is supplied to the step-up converter 174. However, depending on the particular number and arrangement of thermopiles 164, suitable voltage levels are obtained without the step-up transformer. The step-up converter 174 boosts the electrical potential to a suitable level, and provides the output as $V_{OUT}$. In some embodiments, the output has an electric potential of 1.8V, 2.35V, 3.3V, 4.1V, or 5V. Some embodiments supply an electric potential of greater than 2V. Other embodiments supply other electric potentials at $V_{OUT}$.

Figure 5:
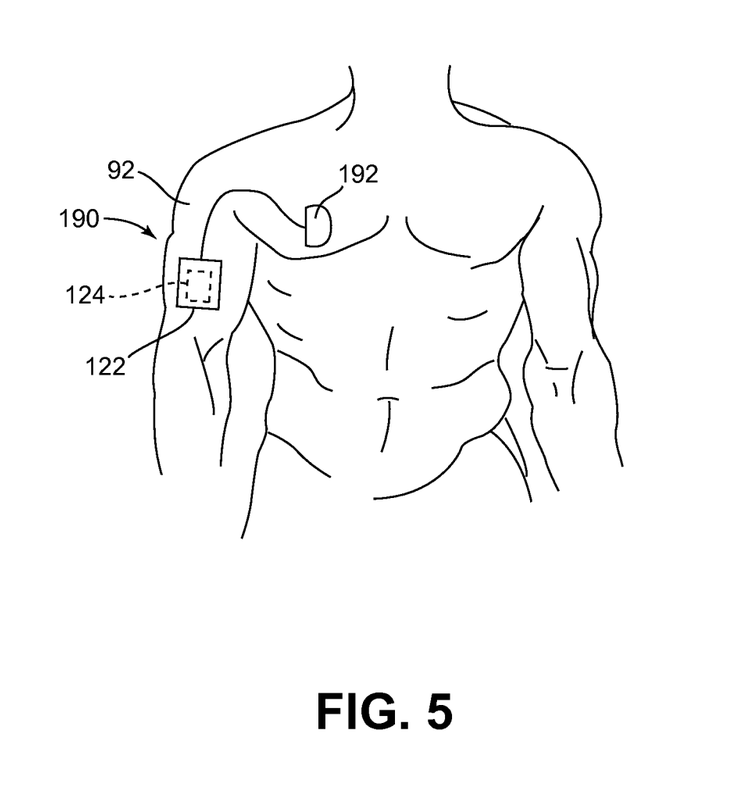
FIG. 5 illustrates another example thermal powered device in the form of a patient-wearable medical device.

FIG. 5 illustrates another example of thermal powered device. More specifically, FIG. 5 is a schematic perspective view of a medical device 190 connected to a living creature. The medical device 190 includes thermoelectric circuitry 122 and an electrical component 192. The thermoelectric circuitry 122 includes a thermoelectric generator 124.

In this example, the medical device 190 is a patient-wearable device, such as a heart monitor where the electrical component 192 includes at least one sensor and a data storage device.

In this example, the thermoelectric generator 124 generates power from a temperature difference between the body 92 of the person and the ambient atmosphere. Even when the patient is in a relatively small room, the patient's body will typically not generate so much heat that the entire room will be warmed to the patient's temperature. As a result, the temperature differential between the ambient atmosphere and the patient's body 92 is sufficient to permit the thermoelectric generator 124 to operate substantially continuously and substantially indefinitely. Accordingly, the medical device 190 is an example of a continuously operating medical device.

Figure 6:
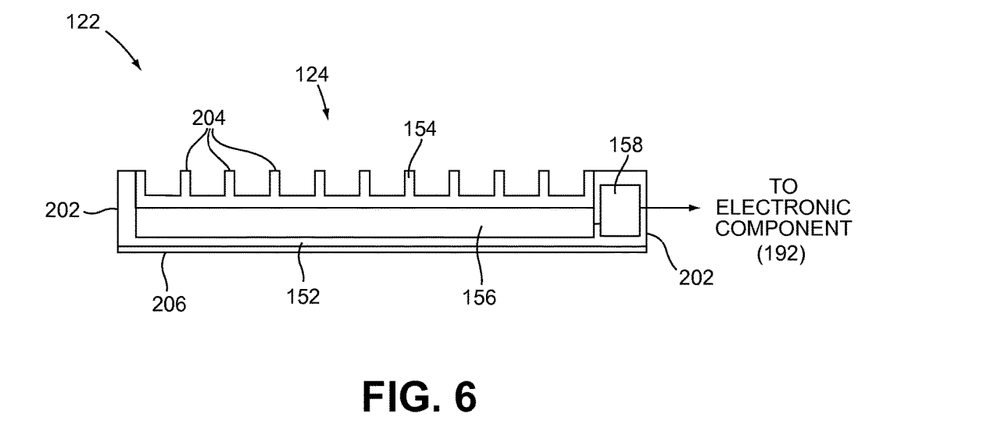
FIG. 6 is a schematic cross-sectional view of an example of thermoelectric circuitry.

FIG. 6 is a schematic cross-sectional view of an example of the thermoelectric circuitry 122 of the example medical device 190, shown in FIG. 5. In this example, the thermoelectric circuitry 122 includes a thermoelectric generator 124 and boost circuit 158.

The thermoelectric generator 124 includes a heat source interface 152, a differential temperature source 154, and a thermoelectric device 156.

The heat source interface 152 is configured to be placed into close proximity to, or direct contact with, body 92. The heat source interface 152 also forms a housing for thermoelectric circuitry 122 in some embodiments, including sidewalls 202 for enclosing edges of the thermoelectric circuitry 122. In an example embodiment, the heat source interface 152 is formed of plastic. Other embodiments utilize other materials, such as metal or other materials. However, it is preferable that at least the sidewalls 202 be made of a material that has a relatively low thermal conductivity. In some embodiments, holes or one or more plates or passages are formed in portions of the heat source interface 152 to permit heat from body 92 to be conducted to the thermoelectric device 156. Accordingly, the heat source interface 152 conducts heat from the patient's body 92 to a portion of the thermoelectric device 156, so that the temperature of the portion of the thermoelectric device 156 is about the same as the temperature of the portion of the body 92. Typical skin surfaces of a human body are about 95 degrees Fahrenheit near the trunk and slightly less for extremities, providing approximately a 90 degree temperature for the heat source interface 152.

The differential temperature source 154 is a heat sink that interacts with the ambient atmosphere. In some embodiments, the differential temperature source 154 includes fins 204 or other features that increase the surface area of the differential temperature source 154 to increase the thermal interaction between the differential temperature source 154 and the ambient atmosphere. The differential temperature source 154 is thermally coupled to a portion of the thermoelectric device 156 so that the temperature of the portion of the thermoelectric device 156 is about the same as the temperature of the ambient atmosphere.

In some embodiments, the differential temperature source 154 is metal with little to no exterior paint. In some embodiments the exterior surface is treated, e.g. by anodizing to a dark color (such as black), to increase emissions of thermal energy. Anodizing to a dark color should reduce internal reflection of IR photons, for example. Treating the interior of differential temperature source 154, e.g. by polishing, to reflect back radiated thermal energy from heat source interface 152 helps keep the differential temperature source 154 cool by reducing absorption of thermal energy.

The thermoelectric device 156 operates to generate electrical energy from the temperature differential between the heat source interface 152 (e.g., 90 degrees) and the differential temperature source 154 (e.g., 70 degrees). Examples of thermoelectric device 156 are described herein, such as one or more thermopiles having multiple thermocouples formed therein. If the surface of thermoelectric device 156 that is proximal to the heat source interface 152 is coated to reflect IR energy, it will tend to protect differential temperature source 154 from thermal radiation.

The output of the thermoelectric device 156 is boosted by the boost circuit 158. Examples of the boost circuit 158 are described herein, such as including a step-up converter 174. Additional electrical components can be included within the housing, if desired, such as a processor, a memory storage device, one or more sensors, or any other desired electrical components.

In some embodiments, the thermoelectric device 156 is provided into a thermally conductive housing, of which a base portion of the housing operates as the heat source interface 152. The housing can have any desired shape, including provision for plates or holes to allow heat transfer. For example, if the thermoelectric device 156 has a square or rectangular shape, the housing may have a similar shape. However, in another possible embodiment, the housing has a different shape, such as a square or rectangular shape with rounded corners, or a circular, oval, or other desired shape. Typically the housing does not fully enclose the thermoelectric device 156 to permit the exterior surface of the differential temperature source 154 to be exposed to the ambient atmosphere and allow the heat source 152 to be exposed to body 92 with low thermal resistance.

The boosted electrical energy is then provided to the one or more electrical components 192 of the medical device 190. For example, the electrical energy can be supplied to a lead that delivers the energy to a patch operable to detect signals from the heart. A wide variety of other medical devices (and associated electrical components) can be similarly powered by the electrical energy in other embodiments.

In some embodiments, the electrical component is a patch including at least one sensing electrode, operable to sense one or more electrical signals in the patient's body. The sensing electrode is coupled to the thermoelectric circuitry 122 by a lead or other electrical conductors, in some embodiments.

The thermoelectric circuitry 122 can be fastened to the body 92 in a variety of ways. For example, thermal adhesive 206 is provided in some embodiments to secure a surface of the thermoelectric circuitry to the skin of the person and provide a low thermal resistance path for heat flux from the body 92 to the heat source 152. In other embodiments, other fasteners are used, such as a strap, band, article of clothing, and the like. Combinations of fasteners such as thermal adhesive 206 and straps may be used. The thermoelectric circuitry 122 can be placed on any portion of the body 92. Keeping the electronics separate from the thermoelectric generator helps keep the differential heat source temperature low; however, with insulation between the electronics and differential temperature source 154, electronics and the thermoelectric device 156 may be disposed in the same housing.

In some embodiments, the medical devices described herein are powered solely by the temperature differential between a living body and the differential temperature source 154. In other embodiments, however, multiple power sources are provided. For example, some embodiments generate power from one, two, or more power sources. Examples of such power sources include, for example, a battery, a capacitor (such as a super capacitor), a solar cell, a mechanical energy harvester, a radioisotope thermoelectric generator, and other power sources. Some embodiments include a multiple-input regulator that operates to add the power from multiple power sources, or to selectively utilize power from one or more of the multiple power sources. In another possible embodiment, the multiple power sources are arranged in series.

In the foregoing description, temperatures are provided in units of degrees Fahrenheit unless otherwise indicated.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A handheld otoscope medical device, comprising:
   an instrument including:
      an adjustable optics assembly;
      an adjustment control configured to adjust a focus of the adjustable optics assembly when a working end of the instrument is placed within a patient's ear canal; and at least one electrical component including a light source positioned to illuminate the ear canal when the working end of the instrument is placed therein; and a power handle with an elongated cylindrical housing sized to be held in a hand of a caregiver, the power handle comprising:
- a mechanical interface that selectively connects the power handle to the instrument;
- an electrical interface that electrically connects the power handle to the electrical component when the power handle is connected to the instrument;
- a solid metallic inner core inside a volume of the cylindrical housing of the power handle and having an outer surface, the inner core encompassing at least a majority of the volume of the cylindrical housing of the power handle;
- a plurality of thermocouples having a first portion thermally connected to the outer surface of the inner core, the plurality of thermocouples being arranged around the outer surface of the inner core;
- at least one thermally conductive layer connected to a second portion of the thermocouples, opposite the inner core, wherein the thermally conductive layer forms at least part of an exterior of the power handle; and
- a boost circuit electrically coupled to the thermocouples and to the electrical interface, wherein the boost circuit receives electrical energy generated by the thermocouples and boosts a voltage of the electrical energy to power the light source of the at least one electrical component.

2. The handheld otoscope medical device of claim 1, wherein the boost circuit comprises a step-up converter integrated circuit and a step-up transformer.

3. The handheld otoscope medical device of claim 1, wherein the housing is a molded plastic housing enclosing at least a portion of the power handle.

4. The handheld otoscope medical device of claim 1, wherein the inner core has a rectangular longitudinal cross section and a square transverse cross section with four sides, and wherein the plurality of thermocouples are arranged around the four sides of the inner core.

5. The handheld otoscope medical device of claim 4, further comprising multiple thermopiles arranged about the outer surface of the inner core, the multiple thermopiles being arranged in series, and each thermopile having a multiple thermocouples arranged in series.

6. The handheld otoscope medical device of claim 5, wherein the thermopiles are positioned in rows on each of the four sides of the inner core.

7. The handheld otoscope medical device of claim 1, wherein the inner core has a solid cylindrical shape, and wherein the plurality of thermocouples are arranged in a radial configuration around the cylindrical shape of the inner core.

8. The handheld otoscope medical device of claim 7, further comprising multiple thermopiles arranged about the outer surface of the inner core, the multiple thermopiles being arranged in series, and each thermopile having a multiple thermocouples arranged in series, and wherein the thermopiles are curved.

9. The handheld otoscope medical device of claim 8, wherein the at least one thermally conductive layer is wrapped around the thermopiles.

* * * * *